United States Patent [19]

Moxey

[11] Patent Number: 5,426,242
[45] Date of Patent: Jun. 20, 1995

[54] POLYETHERS

[75] Inventor: John R. Moxey, Southampton, England

[73] Assignee: International Specialty Chemicals Limited, Southampton, England

[21] Appl. No.: 49,948

[22] Filed: Apr. 20, 1993

[30] Foreign Application Priority Data

Apr. 27, 1992 [GB] United Kingdom ............... 9209079

[51] Int. Cl.$^6$ .......................................... C07C 43/11
[52] U.S. Cl. ................................................. 568/624
[58] Field of Search ..................................... 568/624

[56] References Cited

U.S. PATENT DOCUMENTS 4,676,916 6/1987 Crema .

FOREIGN PATENT DOCUMENTS

| 0074634 | 3/1983 | European Pat. Off. . |
| 0059461 | 9/1992 | European Pat. Off. . |
| 0533165 | 3/1993 | European Pat. Off. . |
| 58-55096K | 4/1983 | Japan . |
| 9005172 | 5/1990 | WIPO . |

*Primary Examiner*—Howard T. Mars
*Attorney, Agent, or Firm*—Brooks Haidt Haffner & Delahunty

[57] ABSTRACT

Compounds of the structure:

$$H(OCH_2CH_2)_kORO\ X_m(CH_2CH_2O)_nH \qquad (I)$$

where R is a divalent hydrocarbyl or hetero-substituted hydrocarbyl
group having up to 10 carbon atoms,
X is $-CH_2CH(R^1)O-$ or $-(CH_2)_4O-$,
$R^1$ is methyl or ethyl,
m is from 0.5 to 3.0 and
k+n is from 3 to 10 the number of X groups not exceeding 25% by weight of the compound are disclosed. Such compounds are useful as hydraulic fluids. R is typically $-(CH_2)_x-$ where x is from 4 to 10. A process for preparing an alkoxylating agent with a diol HOROH in a first step and further reacting the product of the first step with ethylene oxide is also disclosed. A typical diol is 1,6-hexanediol; a typical alkoxylating agent is propylene oxide.

5 Claims, No Drawings

POLYETHERS

The present invention relates to a water soluble polyether of low molecular weight, suitable as a hydraulic fluid and/or lubricant.

There has been a requirement for some time for a water soluble biodegradable base fluid for use especially in mobile hydraulic systems (e.g. for use on vehicles such as tractors, construction vehicles etc.) which may leak fluid to the environment. Organic esters are widely used commercially, but being insoluble in water, unsightly spills which are difficult to disperse can accumulate. Polyethers which are water soluble can also be used as they have the additional advantages of having improved hydrolytic stability, resistance to oxidation and of providing excellent wear protection, thus of providing longer system/fluid life than esters. Commercial products based on copolymers of 50% wt/wt ethylene oxide and 50% propylene oxide (e.g. Breox 50-A grades) have been used. However, despite being of low environmental hazard, these products are only slightly biodegradable.

It is known that polyethoxylates (i.e. polyethers whose alkylene oxide content is 100% based upon ethylene oxide), e.g. Breox PEG 400, are readily biodegradable. However, as a hydraulic base fluid, they suffer the dual disadvantages of high pour point and high density. High density is extremely problematic in hydraulic systems, particularly those where the fluid must be pumped against gravity from the hydraulic reservoir. Many hydraulic systems, designed for use with mineral oil of density of about 0.9 g/ml, can cope with difficulty with densities up to around 1.07 g/ml maximum, and hence densities below this are most desirable.

The problem of pour point can be overcome by using an ethoxylate of propylene glycol, i.e. a polyether made by reacting ethylene oxide with propylene glycol. The methyl group of propylene oxide, giving side branches to the polyether chain, inhibits the biodegradability of polyethers based upon copolymers of 50% wt/wt ethylene oxide and 50% propylene oxide with respect to a polyethoxylate. However, the presence of 1-2 methyl groups, e.g. as with the ethoxylate of propylene glycol or in polyethers based on an ethoxylate of dipropylene glycol or a polyethoxylate with a low concentration of propylene oxide does not have a substantial effect, and the biodegradability remains above 70%. However, the problem of density is not solved.

The overall problem to be solved is to provide a water soluble biodegradable hydraulic fluid with a low pour point and a low density.

Therefore, according to the present invention, there is provided a compound of the structure:

$$H(OCH_2CH_2)_kORO\ X_m(CH_2CH_2O)_nH \quad (I)$$

where R is a divalent hydrocarbyl or hetero-substituted hydrocarbyl
group having up to 10 carbon atoms,
X is $—CH_2CH(R^1)O—$ or $—(CH_2)_4O—$,
$R^1$ is methyl or ethyl,
m is from 0.5 to 3.0 and
k+n is from 3 to 10
the number of X groups not exceeding 25% by weight of the compound.

Block polyoxyalkylene copolymers are known; EP 059461 discloses water-based hydraulic fluids incorporating block propylene oxide/ethylene oxide copolymers, but these copolymers have molecular weights in excess of about 2,000. U.S. Pat. No. 2,674,619 discloses copolymers of propylene oxide and ethylene oxide which are useful as surface active agents and prepared by first condensing propylene oxide with an organic compound containing a plurality of reactive hydrogen atoms to prepare a polyoxypropylene polymer of at least 900 molecular weight and subsequently condensing ethylene oxide or its equivalent therewith. These compounds have either a high propylene oxide content or high molecular weights, i.e. in excess of 2,000.

The advantage of the compounds of structure (I) is that they solve the problems of the prior art, the aforementioned compounds are water soluble and biodegradable and have a sufficiently low pour point and density to be suitable as hydraulic fluids. In the formula (I), R is a divalent linear or branched hydrocarbyl or heterosubstituted hydrocarbyl group having up to 10 carbon atoms, e.g. R is $—(CHR^2)_x$ where $R^2$ is hydrogen or a $C_1$–$C_6$, e.g. $C_1$–$C_3$ alkyl group, preferably methyl, x is such that R has up to 10 carbon atoms and each of the $—(CHR^2)—$ groups can be the same of different; however, R is preferably $—(CH_2)_x—$ (i.e. $R^2$ is hydrogen) where x is from 4 to 10, preferably 6 to 8; m is 0.5 to 3.0, e.g. 0.9 to 2.5, preferably 1 to 2, more preferably about 1; the sum of k and n is from 3 to 10, preferably from 4 to 8. In addition, the quantity of X groups in the molecule is less than 25% wt/wt, preferably less than 15% wt/wt, for example, less than 10% wt/wt.

According to a further aspect of the present invention, there is provided a process for preparing a compound of formula (I) which comprises in a first step reacting an alkoxylating agent which is propylene oxide, butylene oxide or tetrahydrofuran with a diol, HOROH where R is a divalent hydrocarbyl or heterosubstituted hydrocarbyl group having up to 10 carbon atoms in a molar ratio of 0.5 to 3.0:1 alkoxylating agent: diol, optionally in the presence of a base or Lewis acid, and in a second step reacting the product of the first step with ethylene oxide in an amount wherein the molar ratio of ethylene oxide added: diol added in the first step is in the range from 3 to 10:1.

In the process as described herein above, HOROH is a diol where R is a divalent hydrocarbyl or hetero-substituted hydrocarbyl group. A preferred diol is 1,6 hexane diol. The molar ratio of alkoxylating agent:diol is in the range 0.5 to 3.0:1, preferably 0.9 to 2.5:1, more preferably 1.0 to 2.0:1, e.g. 1:1. It is preferred that propylene oxide is reacted with the diol.

Due to the nature of alkoxylation (e.g. propoxylation) it is known and recognised that the diol will substantially alkoxylate on one alcohol group. However, the composition is an average, and will contain a proportion where alkoxylation has taken place on both alcohol groups, and a further proportion of unalkoxylated diol. A substantial majority of these molecules will then be ethoxylated on one or both alcohol groups in the second step.

The first step can be carried out in an inert solvent, e.g. a hydrocarbon such as toluene. However, it is preferred that the alkoxylating agent is reacted in neat diol.

Both first and second steps can be carried out in the presence of a catalyst which is suitably a base, e.g. NaOH, KOH, NaOMe or a Lewis acid, e.g. $BF_3$. When the catalyst is a base the operating temperature for both the first and the second step is preferably in the range 90°–170° C., preferably 105°–140° C. although when a Lewis acid is used as catalyst, the operating temperature can be as low as 40° C., e.g. 25°–60° C., preferably 30° to 50° C.

The process is usually carried out under the vapour pressure of the reactants and/or solvents. In addition, it is preferred to have a small partial pressure of nitrogen in the reaction vessel, e.g. 1–10 bar, preferably 1.5–3.5 bar.

Alternatively, the compound of formula I can be prepared by reacting in a first step an alkali or alkaline earth metal salt of a diol of the formula HOXOH with a compound of the formula Z-R-Y where Z and Y are independently groups capable of forming stable alkali or alkaline earth metal salt and X and R are as defined in formula I above in a molar ratio of 0.5 to 3.0:1 HOXOH:Z-R-Y to give an organic intermediate and an alkali or alkaline earth metal salt and in a second step reacting the organic intermediate from the first step with ethylene oxide wherein the molar ratio of ethylene oxide added :Z-R-Y added in the first step is in the range 3 to 10:1. For example, in the first step a sodium or potassium salt of a diol may be reacted with a dihalide XRX where R is as defined above and X=Br, Cl, I to give an intermediate and a stable salt (e.g. NaCl). The intermediate is then reacted further with ethylene oxide. The man skilled in the art will know what proportions of the reactants should be used to achieve the desired stoichiometry in the final product.

The compounds of the present invention can be used as base fluids especially in mobile hydraulic systems, e.g. on tractors or construction vehicles. Typical additives may also be incorporated into the base fluid, e.g. anti-corrosion, EP/anti-wear, anti-oxidant, anti-foam additives. Therefore, in a further aspect of the present invention there is provided a hydraulic fluid comprising a compound of formula (I) as defined herein above.

The invention will now be illustrated by reference to the following Examples. Breox 50-A-50 is commercially available from International Speciality Chemicals Ltd. Breox PEG 400 is commercially available from BP Chemicals Ltd. "Breox" is a registered trade mark.

Example 1

To 1500 g of 1,6-hexane diol, melted at 60° C., was added 6 g of potassium hydroxide in 6 g of water. The mixture was stripped at 90° C. under 10 mm pressure to remove free water and water of reaction to 0.01% by weight. 1465 g of this catalysed 1,6-hexane diol was transferred to a pressure vessel, and 1080 g of propylene Oxide added over a period of 0.5 hours, and reacted for an additional 1 hour, at 115°–120° C. 2731 g of ethylene oxide was then added over 1.75 hours, and reacted for an additional 1.5 hours, at 115°–120° C. The catalyst was removed by treatment with magnesium silicate to leave a colourless liquid product.

Comparative Examples:

Example A is Breox 50-A-50 which is a polyether having a 50/50 wt/wt ethylene oxide/propylene oxide content.

Example B is Breox PEG 400 which is a polyether based on ethylene oxide as the only alkylene oxide.

Example C is an ethoxylate of propylene glycol (Mol. wt=425).

Example D is a polyether prepared according to the method of Example 1 except that a $C_{12-14}$ diol was used instead of 1,6 hexane diol. (Mol. wt=666).

Example E is Example D diluted with propylene glycol to a viscosity of 47.8 cSt @40° C.

The characteristics of Examples 1 and A-E are shown in Table 1.

TABLE 1

| Example | 1 | A | B | C | D | E |
|---|---|---|---|---|---|---|
| Kinematic viscosity @ 40° C. cSt | 43.5 | 50 | 42 | 40 | 65 | 47.8 |
| Kinematic viscosity @ 100° C. cSt | 7.26 | 11.0 | 7.3 | — | — | — |
| Pour Point °C. | <−18 | −40 | 4 | −33 | — | — |
| Density @ 20° C., g/ml | 1.051 | 1.033 | 1.128 | 1.109 | 0.997 | 1.013 |
| Water Soluble @ 30° C. | Yes | Yes | Yes | Yes | No | No |
| Biodegradability % BOD/COD | 78 | 21 | >80 | 84 | >80 | >80 |
| Flash Point °C. | 225 | 220 | >200 | 235 | >200 | 116 |

In comparison to Example 1:
Example A has poor biodegradability
Example B has a high pour point and a high density
Example C has a high density
Example D has a high viscosity and poor water solubility
Example E has poor water solubility and a low flash point.

I claim:
1. A compound of the structure

$$H(OCH_2CH_2)_k ORO\ X_m(CH_2CH_2O)_n H \qquad (I)$$

where R is a divalent hydrocarbyl of 4 to 10 carbon atoms,
X is —CH$_2$CH(R$^1$)O—
R$^1$ is methyl or ethyl
m is from 0.9 to 2.5 and
k+n is from 3 to 10,
the number of X groups not exceeding 25% by weight of the compound.

2. A compound as claimed in claim 1 wherein R is (CH$^2$)$_x$— and x is an integer from 4 to 10.

3. A compound as claimed in claim 2 wherein x is an integer from 6 to 8.

4. A compound as claimed in claim 1 wherein k+n is from 4 to 8.

5. A compound as claimed claim 1 wherein the number of X groups does not exceed 10% by weight of the compound.

* * * * *

UNITED STATES PATENT AND TRADEMARK OFFICE
CERTIFICATE OF CORRECTION

PATENT NO. : 5,426,242
DATED : June 20, 1995
INVENTOR(S) : JOHN R. MOXEY

It is certified that error appears in the above-indentified patent and that said Letters Patent is hereby corrected as shown below:

Column 4,

Claim 1, line 7, insert a comma (,) after "2.5" and before "and"

Claim 2, line 2, change "$(CH^2)_x$" to $--(CH_2)_x--$

Signed and Sealed this

Twelfth Day of December, 1995

Attest:

BRUCE LEHMAN

Attesting Officer

Commissioner of Patents and Trademarks